(12) United States Patent
Steinhauser et al.

(10) Patent No.: US 11,058,375 B2
(45) Date of Patent: Jul. 13, 2021

(54) X-RAY IMAGING APPARATUS FOR COMPACT (QUASI-)ISOTROPIC MULTI SOURCE X-RAY IMAGING

(71) Applicant: KONINKLIJKE PHILIPS N.V., Eindhoven (NL)

(72) Inventors: Heidrun Steinhauser, Eindhoven (NL); Christiaan Kok, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 228 days.

(21) Appl. No.: 16/305,904

(22) PCT Filed: Jun. 1, 2017

(86) PCT No.: PCT/EP2017/063396
§ 371 (c)(1),
(2) Date: Nov. 30, 2018

(87) PCT Pub. No.: WO2017/207734
PCT Pub. Date: Dec. 7, 2017

(65) Prior Publication Data
US 2020/0315559 A1    Oct. 8, 2020

(30) Foreign Application Priority Data
Jun. 2, 2016  (EP) .................................. 16172577

(51) Int. Cl.
*A61B 6/00*  (2006.01)

(52) U.S. Cl.
CPC .......... *A61B 6/4291* (2013.01); *A61B 6/4007* (2013.01); *A61B 6/484* (2013.01)

(58) Field of Classification Search
CPC . A61L 36/4291; A61L 36/4007; A61L 36/484
USPC ........................................................... 378/62
See application file for complete search history.

(56) References Cited

U.S. PATENT DOCUMENTS

| | | | | |
|---|---|---|---|---|
| 6,222,904 B1* | 4/2001 | Berestov | ................. | A61B 6/022 378/154 |
| 6,438,210 B1* | 8/2002 | Castleberry | ............ | G21K 1/025 378/154 |
| 6,470,072 B1* | 10/2002 | Johnson | ................. | G21K 1/025 378/150 |
| 7,315,640 B1* | 1/2008 | Brady | ..................... | G06T 5/002 382/128 |
| 8,290,118 B2* | 10/2012 | Tsujii | ................... | A61B 6/4007 378/21 |
| 8,666,025 B2 | 3/2014 | Klausz | | |

(Continued)

FOREIGN PATENT DOCUMENTS

| | | |
|---|---|---|
| DE | 545048 C | 2/1932 |
| JP | H105207 A | 1/1998 |

(Continued)

*Primary Examiner* — David P Porta
*Assistant Examiner* — Gisselle M Gutierrez
(74) *Attorney, Agent, or Firm* — Larry Liberchuk (57) ABSTRACT

An X-ray imaging apparatus (IA) having a plurality of X-ray sources (sj) comprising an anti-scatter grid (ASG) for X-ray imaging comprising at least two sets (Mj) of linear x-radiation opaque strips (STj). Each of the strips in the at least two sets have a respective longitudinal axis (Li). There are at least two strips from different sets of the at least two sets that have non-parallel longitudinal axes.

14 Claims, 8 Drawing Sheets

(56) References Cited

U.S. PATENT DOCUMENTS

| | | | |
|---|---|---|---|
| 8,995,613 B2 | 3/2015 | Ouchi | |
| 9,279,775 B2* | 3/2016 | Tsujii | G01N 23/046 |
| 2002/0168052 A1* | 11/2002 | Castleberry | G21K 1/025 |
| | | | 378/154 |
| 2003/0021379 A1 | 1/2003 | Klotz | |
| 2009/0147923 A1 | 6/2009 | Kammel | |
| 2009/0323899 A1 | 12/2009 | Dorscheid | |
| 2010/0246753 A1 | 9/2010 | Mollov | |
| 2010/0310038 A1* | 12/2010 | Behling | A61B 6/4291 |
| | | | 378/9 |
| 2012/0163554 A1* | 6/2012 | Tada | A61B 6/4291 |
| | | | 378/154 |
| 2013/0272505 A1 | 10/2013 | Beck | |
| 2017/0206996 A1* | 7/2017 | Beck | G21K 1/02 |
| 2017/0287582 A1* | 10/2017 | Kotian | A61B 6/4291 |
| 2019/0313989 A1* | 10/2019 | Farbizio | A61B 6/502 |

FOREIGN PATENT DOCUMENTS

| | | |
|---|---|---|
| WO | WO02065480 A1 | 8/2002 |
| WO | WO2012052881 A1 | 4/2012 |
| WO | WO2017144474 A1 | 8/2017 |
| WO | WO2017194727 A1 | 11/2017 |

\* cited by examiner

X-RAY IMAGING APPARATUS FOR COMPACT (QUASI-)ISOTROPIC MULTI SOURCE X-RAY IMAGING

FIELD OF THE INVENTION

The invention relates to an X-ray imaging apparatus.

BACKGROUND OF THE INVENTION

Non-rotational multi-sources X-ray imagers can be used for 3D imaging without complicated mechanics required as in their rotational counterparts, such as C-arm imagers or CT.

Anti-scatter grids (ASG) are used in some of these multi-source X-ray imagers to reduce scatter.

SUMMARY OF THE INVENTION

There may be a need for an improved multi source X-ray imaging apparatus.

The object of the present invention is solved by the subject matter of the independent claims where further embodiments are incorporated in the dependent claims.

According to a first aspect of the invention there is provided an X-ray imaging apparatus (IA) having a plurality of X-ray sources comprising an anti-scatter grid for X-ray imaging comprising at least two sets of linear x-radiation opaque strips, each of the strips in the at least two sets having a respective longitudinal axis, wherein there are at least two strips from different sets of the at least two sets that have non-parallel longitudinal axes.

According to one embodiment, at least one strip from one of the at least two sets is slanted or angled around its longitudinal axes relative to one other strip from said one of the at least two sets. In other words, the strips are focused on a line ("source line") in 3D space where an X-ray source is to be placed for which the respective set of strip can perform a scatter filtering function.

According to one embodiment, the strips in at least one of the at least two sets form a plane. In other words, at least a part of the ASG may be planar or at least includes planar portions.

According to one embodiment, the strips in at least one of the at least two sets form a curved surface. In other words, at least a part of the ASG is curved.

According to one embodiment, the at least two sets are arranged in a common plane. A combination of plane and curved stets are likewise envisaged herein.

According to one embodiment, the anti-scatter grid has at least n≥3 such sets, wherein the respective longitudinal axes of n strips from different ones of the at least n sets form a polygon with n vertices. Specifically, and according to one exemplary embodiment, the anti-scatter grid has three such sets, wherein the respective longitudinal axes of three strips from different ones of the at least three sets form a triangle. Alternatively, the anti-scatter grid has four of such sets, wherein the respective longitudinal axes of four strips from different ones of the at least four sets form a quadrangular.

According to one embodiment, the anti-scatter grid is arranged in front of an X-ray detector of the imaging apparatus. In particular, they may be coupled to a housing of the detector.

In one embodiment there is a single detector that is shared by all of the X-ray sources.

According to one embodiment, there are at least three X-ray sources configured to emit respective X-ray beams towards the detector, wherein the X-ray sources are arranged on or around an optical axis of the detector.

According to one embodiment the at least three X-ray sources are positionable on a plane that does not intersect the detector.

According to one embodiment, the anti-scatter grid is configured to directionally filter in respect of any one of the X-ray beams. In particular, the ASG can be used to reduce scatter in any of the beams propagating through the AGS along different directions from different positions of the X-ray sources.

According to one embodiment, the at least one of the beams irradiates, at the same time, strips from different ones of the at least two of sets. In other words, ASG area is shared by the same beam.

According to one embodiment, the strips are slanted relative to each other so as to focus the anti-scatter grid to a line ("source line") passing through a focal spot of one of X-ray sources of the imaging apparatus.

According to one embodiment, the strips from different ones of the at least two sets are focused to different source lines passing through the focal spots of different X-ray sources of the plurality of X-ray sources.

More specifically, the set of strips is focused towards a source lines that is parallel to the longitudinal axis of the strips in that set, and this source line is generally situated at a given distance away from a front face of the set. This distance may differ for different stets.

Each set corresponds to different sub-grids or modules of the (composite or "super")-ASG. Having the strips from the at least two sets extend respectively along non-parallel longitudinal axes which allows definition of at least two intersecting source lines in 3D to establish one or more intersection points. The source lines are defined by the mutual angulation of the strips in the set. Positioning, as is done in one embodiment, sources on respective ones of these one or more intersection points allows sharing ASG area by a beam from said source. In other words, the same X-ray source can be scatter filtered by parts of the strips in different sets of which allows decreasing the footprint of the anti-scatter grid as there is no requirement to have a dedicated sub-area of the anti-scatter grid filter only for one and only one of the plurality of X-ray sources. This in turn leads to an overall more compact design of the whole imaging apparatus.

The proposed grid is of particular application in systems where the plural sources are laid out in a 2-dimensional configuration (rather than the sources being lined up in "1D" in a sequence along a straight or curved line) which usual yield a range of markedly different projection angles.

It should be noted in the above that a set of strips usually corresponds to a module or sub-grid of the ASG, but this is not necessarily so in all embodiments, where two (or more) sets of strips with their respective longitudinal axes at different orientations are part of the same/single module.

The following notations are adopted herein:
sj: j-th X-ray source;
Bj: beam emitted from source sj;
bj: area on ASG irradiated by beam Bj;
Mj: ASG module or set of strips therein;
STj: strip of module Mj;
slj: source line generated by ASG module Mj.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
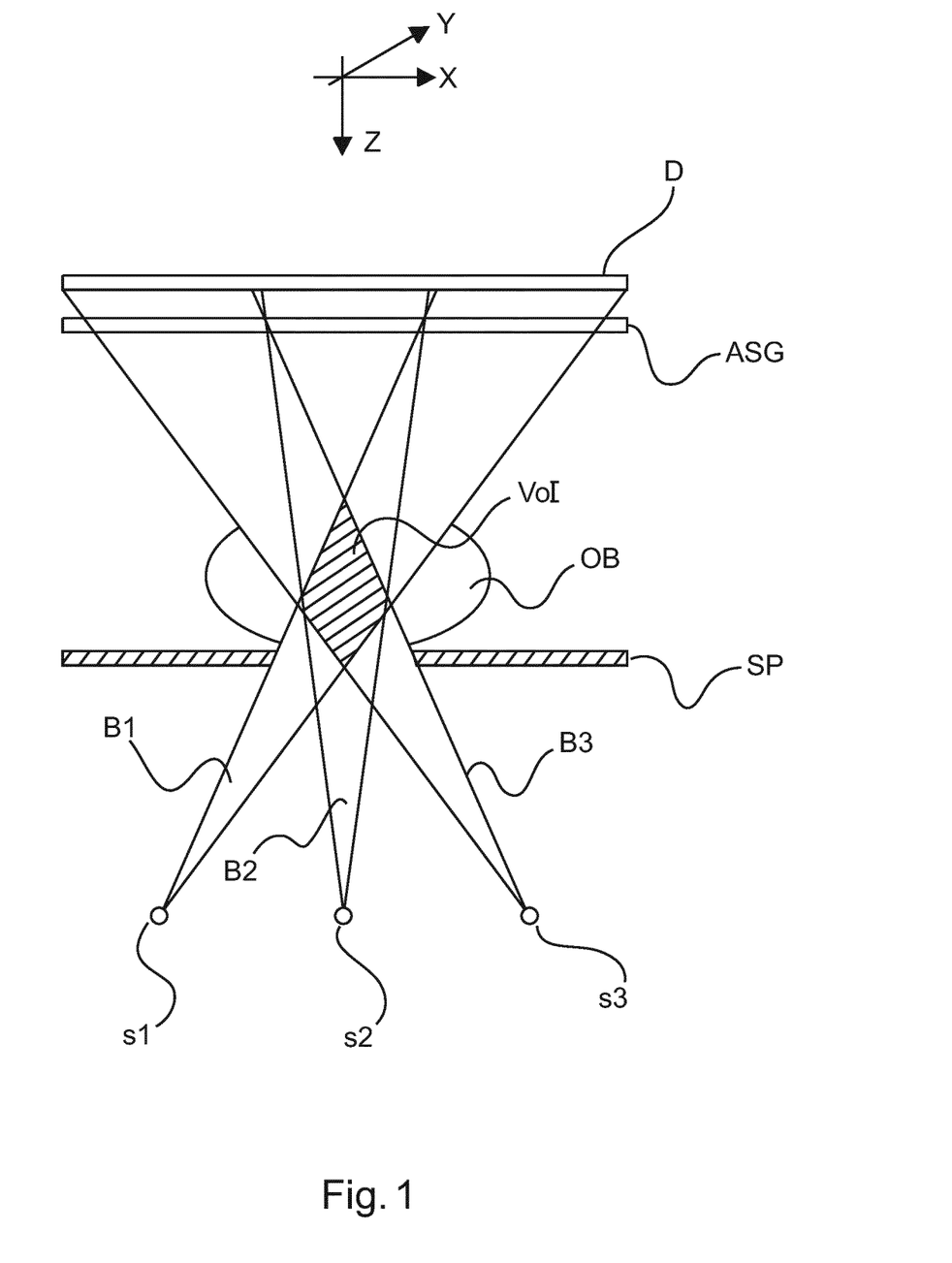
FIG. 1 shows a multi-source imaging apparatus.

With reference to FIG. 1 there is shown a schematic side view of some components of a multi-source X-ray imaging apparatus IA. The imaging apparatus IA comprises three or more X-ray sources sj (only three X-ray sources s1, s2 and s3 are shown but this is not limiting) operable to emit respective X-ray beams B1, B2 and B3 towards an X-ray detector D. A shape of the beams can be shaped by an optional pre-collimator (not shown). The beams Bj are preferably cone beam but fan beams are also envisaged. Furthermore, parallel projection beams may also be envisaged herein in alternative embodiments.

The detector D comprises a radiation sensitive surface made up from detector pixels. In an examination or imaging region in between the sources sj and the detector D there is disposed an object to be imaged OB such as a human or animal patient or an anatomic part thereof supported on support surface SP such as a patient bed, examination table or the like. Although the imaging apparatus IA can be used for purely 2D projective radiography, 3D imaging is envisaged herein as a preferred embodiment. To this end thanks to the plurality of X-ray sources sj arranged around the examination region, a plurality of different projection images 7E are acquired from different projection directions (corresponding to the different propagation directions of the X-ray beams B1-B3). The projection imagery 7E can then be reconstructed by available algorithms into a 3D image volume of that part of the object OB that resides in a volume of interest VOI. The VOI is defined as the intersection in 3D space of all beams or at least two thereof. It is not necessarily herein that all X-ray sources operate simultaneously. Imaging proceeds broadly as follows: the X-ray beams Bj travelling through the matter in the object OB are modified. It is this modified radiation that impinges on the detector pixels. The impinging radiation causes electrical signals (by direct or indirect conversion) at the individual detector pixels. The signals can be converted by AD circuitry into the respective projection images π. These can then be processed by a 3D reconstruction algorithm to produce 3D imagery which can then be rendered for view on a monitor, stored for later use or can be otherwise processed. Absorption imaging, phase contrast imaging and dark field imaging (also known as small scatter imaging) are all envisaged herein in different embodiments. For the latter two imaging applications, an interferometer (not shown) is usually required as an additional piece of equipment in the imaging apparatus IA.

The X-ray imaging apparatus IA can be seen to be of a two dimensional wide angle multi-source imaging type. That is, the plural sources are not all linearly arranged in a sequence along a line (straight or curved) but define a layout in 2 dimensions around the object which requires relatively large projection angles differences as compared to a purely linear source layout. It uses in particular stationary X-ray sources, so the different sources are arranged in a fixed mechanical construction (such as a frame or the like) around the detector and are not rotational. Although it is envisaged in one embodiment that the sources are motorized or can be manually moved into different positions around the X-ray source, there is no motion during the imaging as is in the case in rotational systems such as CT or C-arm imaging. This allows reducing the mechanical overhead that these rotational systems necessitate. In simple embodiments the X-ray detectors are not moveable by the operator and are permanently fixed in a fixed geometrical arrangement around the object OB to be imaged.

The digital X-ray detector D is in general a flat panel detector having a flat rectangular shape (as in FIG. 1) in a housing which is suitably mounted above the object to be imaged. Alternatively, a detector with a curved radiation sensitive is also envisaged. The detector may be ceiling mounted, floor mounted as the case may be. Although only a single detector D with single radiation sensitive surface is shown in FIG. 1 as the preferred embodiment, other embodiments with multiple detector units are not necessarily excluded herein.

It will be beneficial in the following to introduce a co-ordinate system to indicate the various locations and directions involved with the components shown in FIG. 1. Axes X, Y define a horizontal object plane on which resides the object OB to be imaged. That plane extends into the plane of the drawing in FIG. 1. Generally these axes are parallel to the respective edges of the patient support SP.

There is also an image plane defined by the detector D's radiation sensitive surface and in general this plane is parallel to the X, Y plane or at least to a tangent plane in case of a curved detector.

Perpendicular to the image plane, through a central point of the detector sensitive surface and through the object plane runs a main optical axes Z of the imager. Ideally, this axis Z passes through the volume of interest VOI, preferably centrally. Spatio-relational terms as used herein such as "in front" or "behind", "downstream", "upstream", etc will be taken relative to the propagation directions of the X-ray beams Bj.

The X-ray sources sj (sometimes simply referred to herein as "sources") are arranged opposite the detector D, across the examination region, Specifically, and in the (preferred) embodiment in FIG. 1, the sources sj are located (relative to the gravitational field) under the object OB (or object support SP) to be imaged whilst the detector is located above. The specific geometry shown in FIG. 1 is not limiting, as a geometry reverse to the one shown in FIG. 1 is also envisaged, where, relative to gravity, it is the detector that is mounted below the object or object support and, accordingly, the X-ray sources are mounted above (relative to the gravitational field) the object/support. It will be appreciated however, that the above introduced co-ordinate system and the spatial relational terms are invariant to such a re-arrangement and applicable to both of these embodiments.

The X-ray sources sj are generally grouped around the main optical axis of the detector in a number of different (geometric) source configurations (as referred to herein as "source geometry") such as circular, elliptic or polygonal when viewed along the Z axis. The geometric source configuration may be defined by an envelope curve that passes through some (or all) source locations. In some embodiments one or more of the sources sj may be located inside the envelope curve formed by the remaining sources. In addition or instead, the sources may be arranged linearly along a single or along plural lines.

Preferably, the geometric configuration is symmetric around the main optical axis Z through the VOI and at least some of the sources are preferably equi-angularly ("isotropic") distributed around the VOI/optical axis Z. Although such an equi-angular or isotropic arrangement around the VOI is the preferred spatial embodiment, quasi-isotropic arrangements are also envisaged herein where the source arrangement varies from a strict equi-angular arrangement. The source arrangement is preferably symmetric relative to the object but this is not necessarily so in all embodiments as asymmetric arrangements are also envisaged. In some embodiments (but not necessarily in all embodiments), if the arrangement is asymmetric or merely quasi-isotropic, there is at least a symmetric or isotropic sub-set of sources. In other words, an otherwise isotropic or symmetric arrangement can be enlarged by placing additional sources on the source lines as required in different use scenarios. This (at least quasi-) isotropic source geometry has been found to allow good 3D reconstruction or 4D reconstruction (being a time series of 3D reconstructions). The X-ray sources sj are operable to project their respective beams Bj along different directions from below (or above) at an angle onto the X-radiation sensitive surface. In addition there may be a central source s5 that affords an AP view on the object. The central source is located below the object OB/object support SP and on the central axis Z to emit a beam B along said axis Z.

In one embodiment, but not necessarily in all embodiments, all the X-ray sources sj are located in a plane ("source plane") with the optical axis being normal to said plane although angular source planes are also envisaged herein. The VOI/object of interest does not intersect the source plane. Furthermore, in the imagers IA envisaged herein, the detector plane is different from the source plane, in particular the detector does not intersect said source plane. Also, as mentioned earlier, the sources sj are in general fixed and are not moveable although there are embodiments envisaged where at least one or more than one or all sources can be linearly translated and/or re-oriented to change the layout of the sources and hence the source geometry. The locations of the sources sj are not necessarily confined to a plane, but may be located at different z positions parallel to Z. For instance, sources with steeper (longer in-tissue path length of the beam) projection direction relative to the object OB may require stronger intensity sources and these may then be placed closer, "out-of-plane", to the patient than more distal, weaker sources.

The imaging apparatus IA further comprises an anti-scatter grid ASG (which will likewise be referred to herein as ASG) which is situated in front of the detector, specifically between the object and detector D's X-ray sensitive surface. The anti-scatter grid forms a surface ("ASG surface") which is in general co-extensive in shape and size with that of the detector sensitive surface. In other words, the ASG can be a curved surface or a plane. The ASG is mounted on the detector itself, but this is not necessarily the case, or it is mounted spaced apart by mounting members away from the detector.

The function of the ASG is to increase image quality. In particular in absorption imaging, the signals detected at the detector D correspond to the attenuation (that is, the loss of intensity) experienced by the X-ray beams Bj as they pass through matter of the object OB to be imaged. Ideally, this attenuation should be fully attributable to absorption events. However, in reality this is not true: not all of the attenuation is attributable to absorption (that is photo-electric absorption) as there is also a contribution from scatter. In other words, the electrical signals recorded in response to impinging X-ray radiation should be fully attributable to absorption. The function of the anti-scatter grid ASG then is to remove or at least diminish said scatter contribution. The AGS acts as a directional filter in respect of the X-ray beams B1-B3. More specifically, the ASG is configured to filter individual photons for a given source sj according to the trajectory orientation of the photons. That is, preferentially, X-rays emanating from the focal spot of source sj are capable of passing through the ASG while the ASG tends to at least partly block all other "rogue" X-rays that originate from scatter events. Geometrically speaking and as indicated in FIG. 1, an irradiation volume can be defined by drawing a set of geometrical rays emanating from the focal spot FSj towards the detector. The anti-scatter grid is so configured that it allows only radiation to pass through it that travels along any of the geometrical lines within the pre-defined geometrical irradiation volume.

Broadly, the novel anti-scatter grid ASG as proposed herein is configured to perform its directional filter function as a single unity for any one of the different X-ray beams Bj emittable by the plurality of X-ray sources sj located at different locations in 3D space.

Referring now again to the exemplary geometry shown in FIG. 1, it can be seen that different X-ray beams Bj irradiate different sub areas bj of the whole detector surface. In other words, the irradiated sub areas are disjoint. However, this may not be necessarily so in all embodiments, as it has been observed that a more compact construction of the X-ray imager IA can be achieved when different X-ray sources from different positions share the same sub-area or at least where there is a geometric intersection between the different sub areas so irradiated. This detector-area sharing by different sources sj is not necessary but is a preferable embodiment of the apparatus IA proposed herein. The novel anti-scatter grid allows achieving detector area sharing, and it is configured to function as a joint or common, single ASG unit even when different ones of the X-ray sources use the same sub area or when there is an intersection of irradiated detector areas from different sources.

Figure 2:
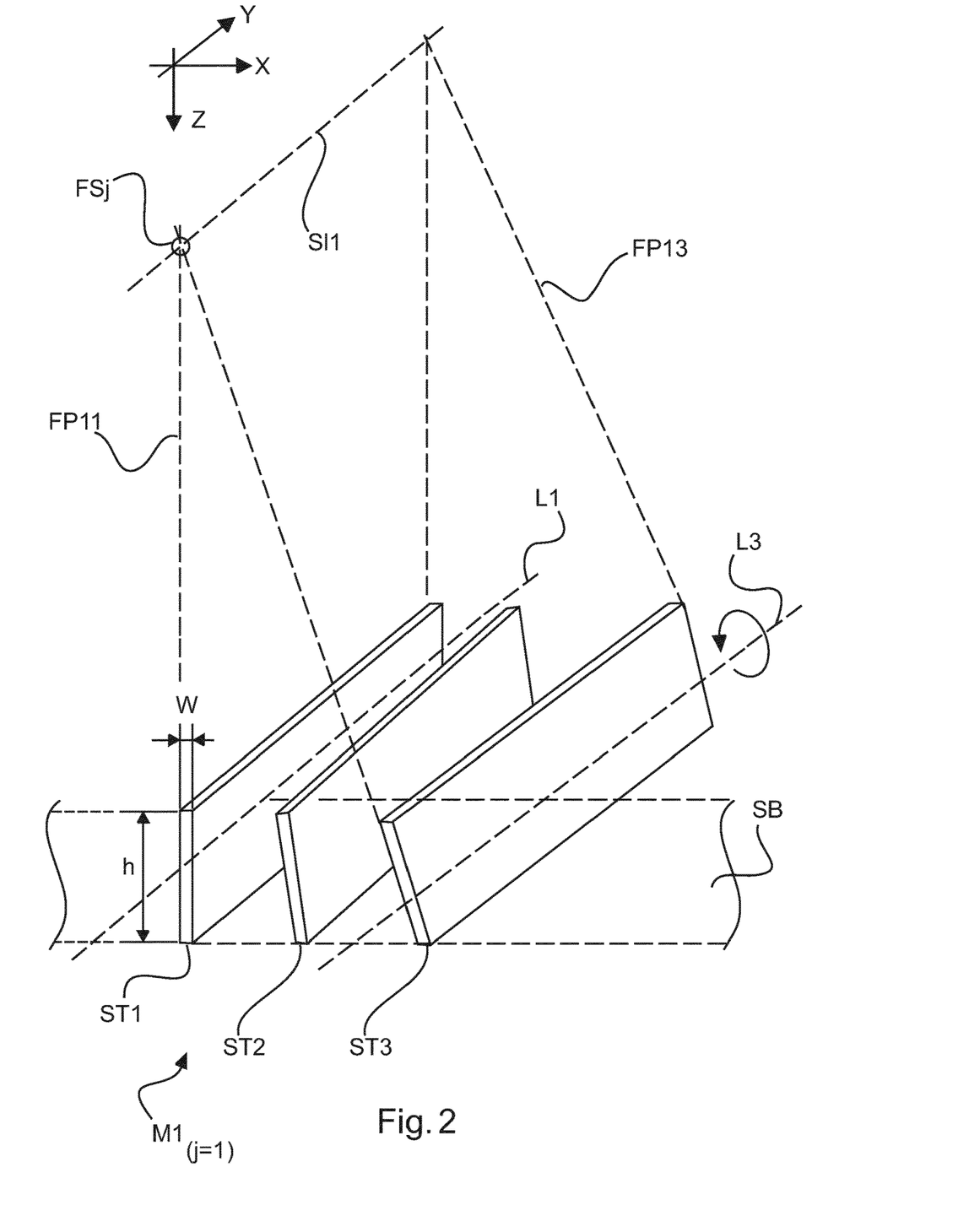
FIG. 2 shows a perspective view of a part of an anti-scatter-grid as used in the X-ray imaging apparatus of FIG. 1.

In order to better explain how this shared ASG functionality is achieved constructionally, reference is now made to FIG. 2. The proposed anti-scatter grid ASG is envisaged as an assembly of different (that is 2 or more) grid parts or grid modules or panels Mj. FIG. 2 illustrates in perspective view a part of one such grid module (Mj, j=1 as a matter of example). Each module comprises a set or series of flat, radiation opaque strips or "lamellae". This set of discrete strips is formed from lead, tungsten or an alloy or from other metals or materials of suitably high Z materials to essentially block out X-ray. Because each module Mj is uniquely defined by its strips STj we will use the notation "Mj" interchangeably for the set of strips as well).

The longitudinal strips STj are arranged in alternation with corresponding strips of buffer or filler material SB in between any two adjacent strips. Only three strips ST11, ST12, ST13 are shown for illustration in FIG. 2, it being understood that there are usually more than three strips). The buffer material SB is formed from X-ray radiation translucent material such as cellulose (eg, cardboard/paper) or aluminium or other. In other words, the buffer material is for structural integrity of the module but is configured to award essentially undisturbed passage through the ASG module. The buffer strips are in the order of $\frac{1}{10}^{th}$ of a Millimeter thick (eg, about 0.1-0.3 mm) but this number is merely an illustrative example.

Each strip has a height, H, a thickness W and a longitudinal axis that extends along the longest edge. For illustration, the strips are in one exemplary embodiment in the order of 100s of Millimeters long (eg, 400 mm), about in the order of $\frac{1}{100}^{th}$ of a Millimeter thick (eg, 0.03 mm) and about in the order of Millimeters high (eg, 2 mm). There are about 1000-2000 strips to the module, eg about 1500 or 1600. All these numbers are purely exemplary and will depend in the specifics of the imaging apparatus IA at hand. The longitudinal axis of the different strips are shown as a L1, L3 (L2 is not shown). The longitudinal axes of the strips for a given module are parallel to each other. Some, but not necessarily all, of the strips are angled or slanted relative to each other and around their respective longitudinal axes as shown conceptually by angle $\alpha$ in FIG. 2. Despite the angulations, the strips are laid out in plane, that is, the longitudinal axes are all located in a plane. This arrangement gives rise to a flat or planar ASG module/panel. Alternatively, curved ASG modules Mj are also envisaged where the longitudinal axes although parallel, are not located in the same plane thus defining a non-planar or curved ASG grid module.

This mutual angulation allows focussing the strips to the focal spot FSi of a specific one of the X-ray sources sj. In this sense, each module Mi with its set of strips, is associable with one of the plurality of X-ray sources sj. More specifically, and explaining the focusing geometry in more detail, each strip can be understood as a segment of a plane (focal plane) FPij in which this strip lies. It is also the respective longitudinal axis that lies in the respective plane. Because of the angulations, these planes FPij will intersect in a line that passes through the focal spot FSj of the associated X-ray source sj. This line formed by the intersection of the focal planes in which the respective strips of a given Module lie, is referred to herein as a "source line" $sl_j$. It is via its source line that the respective ASG module is associable in 3D space with a location of a certain X-ray source sj. More specifically, the specific geometrical orientation of the plurality of strips in a given module give rise to a source line in 3D space and the said module can perform its ASG function for any X-ray source whose focal spot happens to lie on this source line or, equivalently, for different locations on said source line for the same source sj. In other words, this association relation between the X-ray source sj and ASG module Mj is not 1:1 but many-to −1. There are embodiments envisaged wherein where more than one source sj is located on the same source line slj. The strip angulations and orientation of the strips' longitudinal axes uniquely determine the location in 3D of the source line sj. In particular, the orientation of the strips' longitudinal (relative to a world coordinate frame) uniquely determine the orientation of the source line for a given grid module Mj. It is therefore apt and convenient to speak of a "source line orientation of module Mj". When two modules Mj,Mk in a given plane have different source line orientations this means that the longitudinal axes of their respective strips STi, STk are different, that is, they are non-parallel. It should be noted that a distance from the module to its source line slj may differ for different modules Mi.

The strip angulations can be "symmetric" or "asymmetric". In symmetric angulation (as shown in FIG. 2), there is no angulation at the center strip and the angulation of the remaining strips is the stronger, the further away the strip is located from the center strip, with all strips to the left of the center strip angulated clockwise whilst all strips to the right are angulated counter-clockwise. In asymmetric angulation there is no non-angulated center strip, that is, all strips are angulated either counter-clockwise or clockwise. A consequence of this is that, for a given symmetric module Mj, the orthogonal projection of its source line onto the plane of the module falls within the center of the module's Mj area (that is the area covered by its strips STj). For an asymmetric module this is not the case. Here, the orthogonal projection of the source line is off-center or may fall outside the grid module's Mj area. That is, asymmetric grid module allows defining its source line "away" or "sideways" from where the module Mj itself is located.

The ASG proposed herein includes a plurality of such grid modules of the kind shown in FIG. 2 arranged adjacent to each other to form the ASG as a single super-grid as it were. More specifically, it is proposed herein an ASG that includes a plurality of strip modules Mi such that there are at least two grid modules Mi, Mj with their respective strips having non-parallel longitudinal axes. The ASG is thus configured to generate different source lines and the very same ASG is capable of providing ASG functionality for a plurality of different X-ray sources whose focal spots are distributed in space, so long as any one of these focal spots of these sources lie on at least one of the source lines. In other words, a single ASG grid (made up as an assembly of modular grids Mj) can support very complicated source geometries distributed in 3D. Moreover, the ASG is configured to produce intersecting source lines. Placing a source on an intersection point of two (or more) source lines allows sharing ASG area. In other words, a beam from the source at the intersection point is filtered jointly by the two modules that generate the intersecting source lines. This allows reducing the overall footprint of the ASG and hence of the imager as a whole. In the following FIGS. 3-7 are illustrated a variety of source sj geometries, each with a respective supporting ASG strip geometry according to different embodiments all envisaged herein. The view afforded in the following Figures on the ASG is along the optical axis Z in plan view from above, with the detector D, object OB and support surface SP cut away for ease of presentation unless described otherwise. All of the below is of equal application for imagers in reverse geometry (source above and detector below object).

Figure 3:
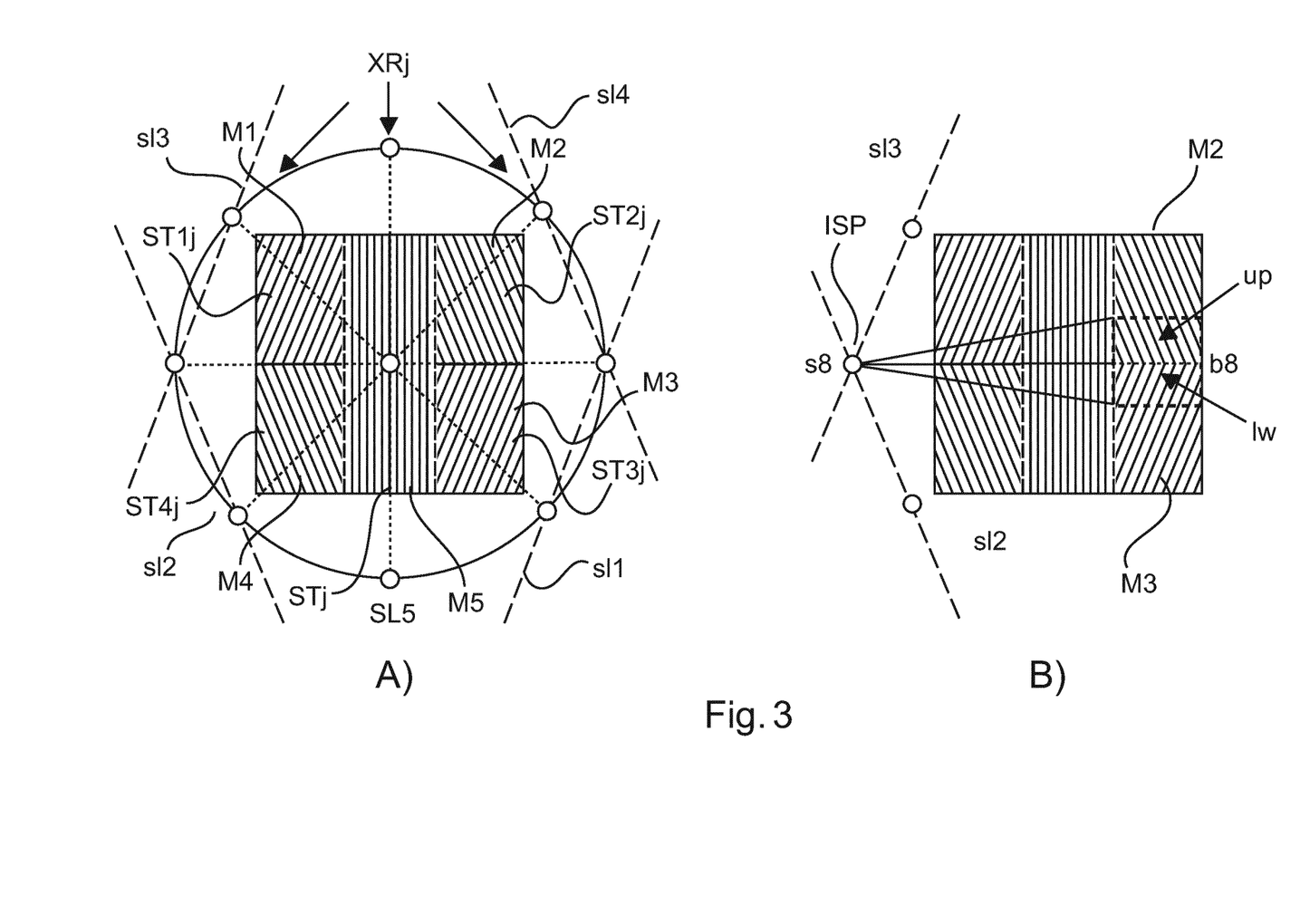
FIGS. 3-8 show different embodiments of different anti-scatter grids.

Referring now to FIG. 3 in more detail, there is shown an ASG configured from multi-source imaging according to one embodiment.

The overall layout of the ASG in plan view Z is rectangular, in particular, square, but any other quadrangular or polygonal or in fact circular or elliptic layout is also envisaged in alternative embodiments. In FIG. 3A, B the grid ASG is planar. The particular ASG shown in FIG. 3 includes five sets M1-5 with different source line orientations. 4 modules M1-M4 are grouped around a center module M5. The course of the longitudinal axes of the strips are shown in this and the following FIGS. 4-7 in different hatchings, with the orientation of the hatching representing the orientation of the longitudinal axes. The corresponding source lines generated by these modules Mj (j=1-5) are indicated as slj (j=1-5).

It will be understood that having five sets of ASG strips as shown in FIG. 3 is merely according to one embodiment and other numbers of modules per AGS less than five or more than five are also envisaged. The number of modules Mj per ASG is a function of the number of X-ray sources to be used. This number is less than or equal the number of sources. Because of the intersecting source lines and the fact that one can place several sources on the same source line, this number is preferably less.

In the embodiment as shown, there are five grids M1-M5 versus eight sources s1-s8. The X-ray sources sj are shown as dots arranged in a circular source geometry around the axis Z of the grid. In a specific embodiment in FIG. 3, there are eight X-ray sources arranged around the axis Z with an additional, center, X-ray source, s8 arranged on the axis Z above or below the patient. This central source s8 affords imaging in AP (anterior posterior) or PA view.

Modules M2, M3 generate source lines sl2,sl3 of different orientation and thus have their strips run in non-parallel directions and so do Modules M1,M4. However, the opposing pairs modules M2,M4 and M3,M1 have source lines of respectively same orientation. FIG. 3 is hence an embodiment where not all modules have source lines with different orientation. Other, alternative embodiments, are also envisaged where there are no two modules having source lines with same orientation.

The longitudinal axis of the respective strips of set M1 and M4 and M3 and M2 and thus their source lines together form a quadrangle, in particular a lozenge shape if the dashed lines are followed through to their respective intersections.

It can be first seen from FIG. 3, that the strips in the peripheral, outer modules M1-M4 are so focused that the respective source line is not situated directly perpendicular under the respective set MI but is slightly off-set to the side further away from the optical axis Z. This allows locating the source lines further away from the patient table. Having the source line located closer to the optical axis Z will allow building an image apparatus with a smaller footprint. In other words, the peripheral modules M1-4 are asymmetric whilst the center grid M5 is symmetric.

Each sub-grid Mj filters for those X-ray sources that lie on its corresponding source line. The ASG as envisaged in FIG. 3 includes sub-grids such as M2 and M3 whose source lines sl2,sl3 are intersecting. In other words, X-ray source s8 located at this intersection will have its beam B8 filtered jointly by both sub-grids M2, M3. In other words, this is an example mentioned above where filter action is shared among two grids for the same X-ray source. X-ray source s8 situated at 9 o'clock on the intersection of source lines sl3 and sl2 has its beam filtered by respective sub-sets of strips in sub-grid M2 and sub-grid M3. The same is true for grids M1, M4 in relation to the X-ray source situated at 3 o'clock on the intersection of source lines sl4 and sl1.

The center sub-grid M5 filters the beam emitted by AP X-ray source situated under the patient table (or above in reverse geometry).

The ASG is preferably formed as a unitary whole from the different sub-grids M1-M5 with respective strips from different modules meeting at an angle as shown for M2,M3 and M1,M4.

The grid sharing as proposed herein is shown in more detail in FIG. 3B. Source s8 is situated at the intersection ISP of the source line sl3 and Sl2. Beam B8 emitted from said source is ASG filtered by sub-grids M2 and M3. Beam B8 irradiates an area b8 that covers portions of both grid M2 and grid M3. The sub-set of strips irradiated in M2 is indicated as "UP" whereas the sub-set of strips irradiated in grid M3 by the same beam B8 is shown as "LW".

The position of each source in FIG. 3 can be shifted along the source lines, and any of the source geometries obtained in this manner will then still be supported in terms of ASG function by the very same ASG grid. It is therefore not necessary to redesign the ASG grid for different source geometries, so long as each source lies on at least one of the source lines. In yet other words, the set of all possible X-ray source arrangements that are supported by a given grid ASG is defined by the system of its source lines. Having source line configurations with intersection points is preferable and this results in sharing ASG area as shown in FIG. 3B.

All of the sub-grids in FIG. 3 are all quadrangular in particular rectangular. This may not always be the case, as other geometrical shapes such as triangular or other polygonal shapes can be used and the ASG can then be built up as a tiling from these sub-grids in a combination of same or different shapes. Specifically, in FIG. 3 the ASG is a tiling of rectangle shaped sub-grids M1-5.

More than two source lines (three or more) may intersect as shown in FIG. 3A, eg the source line sl5 of the center sub-grid M5 and source lines sl2, sl1. Positioning a further source at this intersection point (not shown) will result in having its beam ASG filtered by three sub-grids jointly, namely by center grid M5 and sub-grids M1 and M2.

Figure 4:
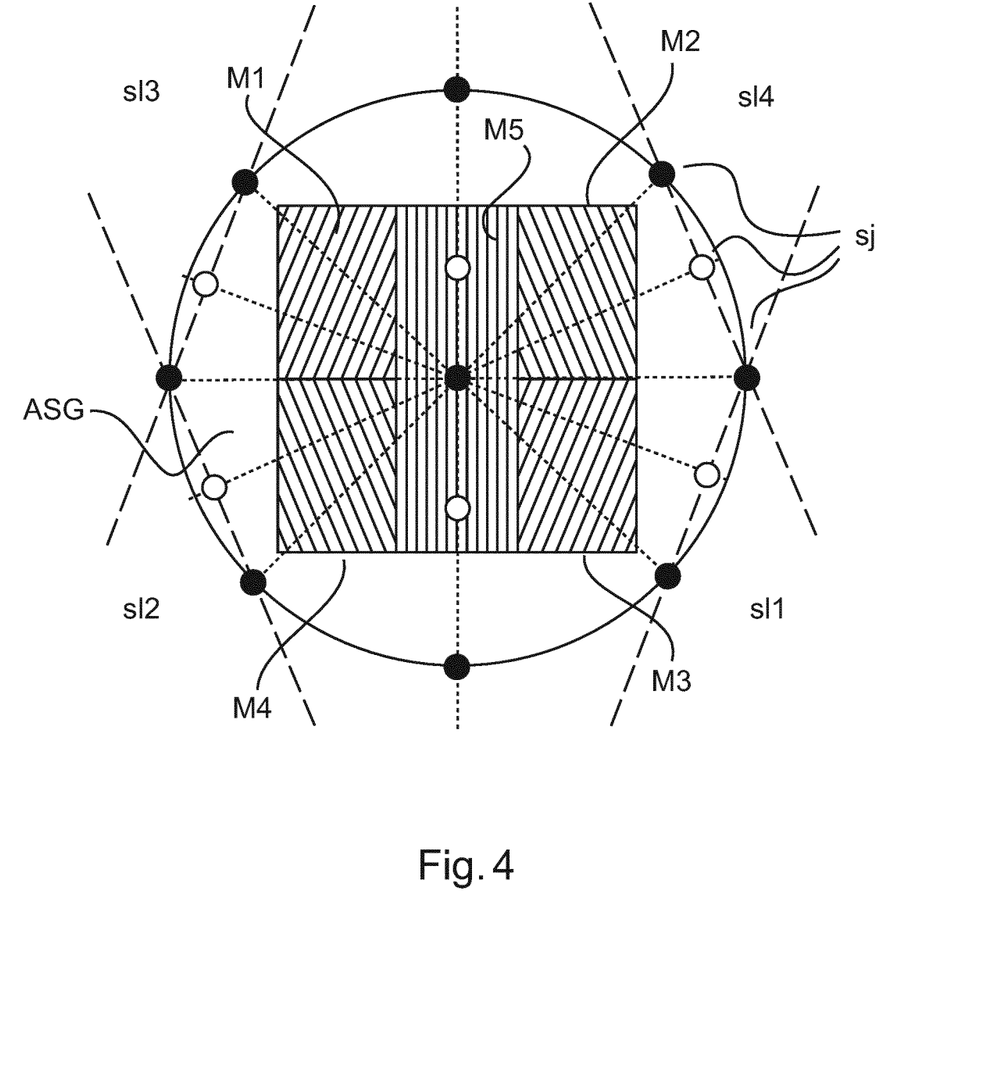

Reference is now made to FIG. 4, which shows a similar ASG to the one in FIG. 3 in circular source geometry for an imager IA having fifteen X-ray sources s1-s15. Compared to FIG. 3, six additional sources have been added (shown as light dots), two onto the source line sl5 of center grid M5 and to either side of center source M5, and four other sources have been placed, respectively, on the four source lines sl1-sl4. The envelope of the source positions in plan view is circular around the optical axis. On each peripheral source line there are now located 3 sources, with 4 sources being located symmetrical on the center grid's source line sl5, with one source on the center axis Z with the 4 other off-set therefrom, with 2 sources on either side.

As in this and all the remaining embodiments, the source line of the center grid M5 runs parallel to a longitudinal axis of the patient support, whilst in other embodiments the center grid source line runs across. This later arrangement is obtained by rotation of the ASG in FIGS. 3, 4 and 5 by 90° clockwise or anti-clockwise. Again, central grid M5 is symmetric whilst the remaining ones are antisymmetric. The above is not confined to 90° rotations, as embodiments of the ASG obtainable by rotations any other than by 90° are also envisaged herein.

Figure 5:
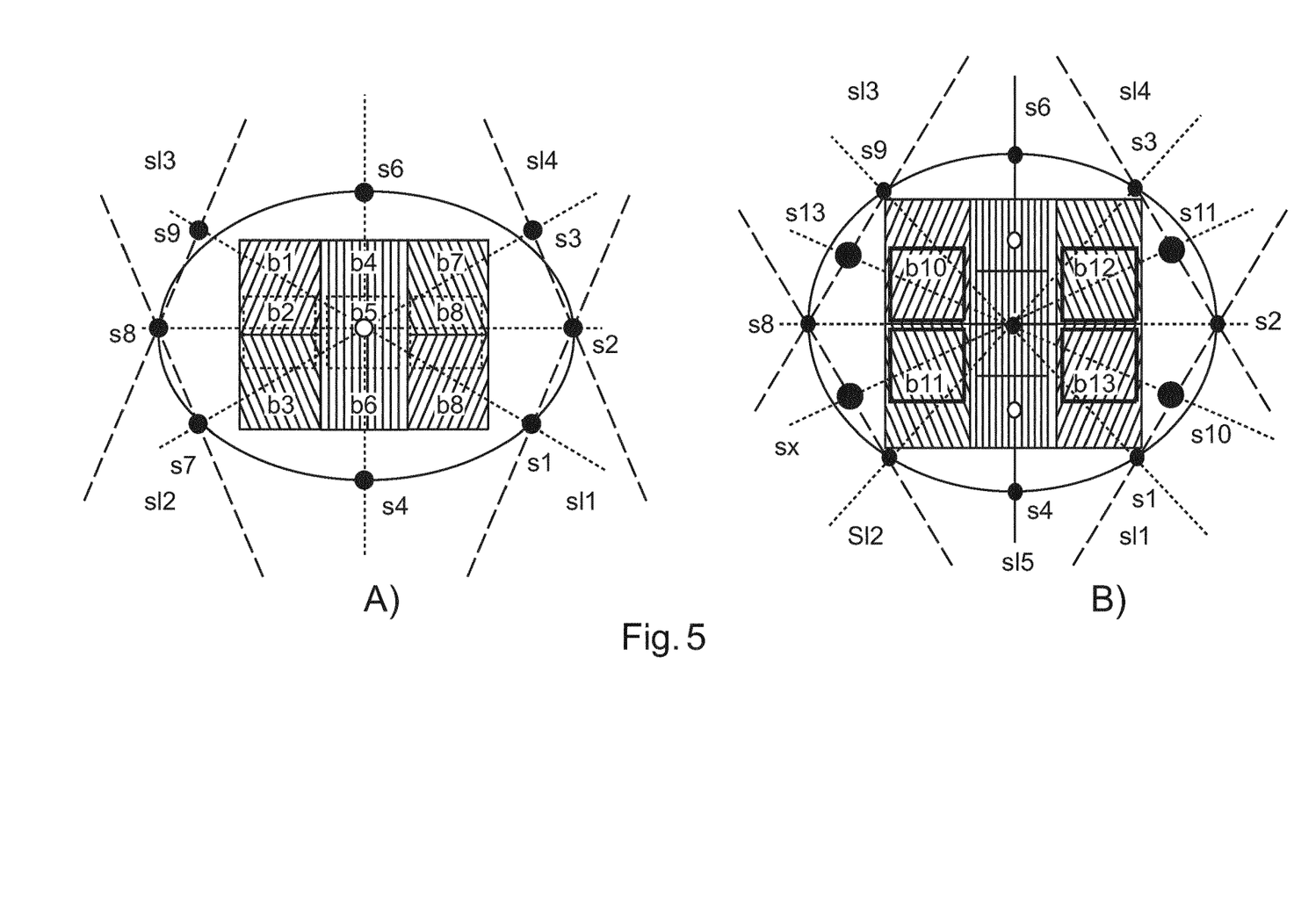

Reference is now made to FIG. 5 showing another source geometry, but now in elliptic layout with nine sources s1-s9 in FIG. 5A whilst in FIG. 5B there are fifteen sources s1-s15 used. The ASG is similar to the one described above with 4 peripheral grids M1-M4 and one center grid M5 for AP view imaging. The shape of ASG in FIG. 5A is planar rectangular, whilst the one in FIG. 5B is planar square. There are 5 source lines sl1-sl5 generated by these sources s1-s5, defining a lozenge shape with 4 intersection points. The bj indicates as before the respective area of the sub-grids irradiated by source sj. For instance, b5 indicates the area of the center grid irradiated by source s5 situated below or above the ASG whilst rectangle b7 indicates the area irradiated by source S7 and filtered by S8.

There is again sub-grid sharing in this exemplary embodiment as can be seen by the sources situated in source line intersection points, eg sources s2 and S8 in FIG. 5A, B. The respective shared areas are shown as b8 and b2. The source geometry in FIG. 5B is obtained from the one in FIG. 5A by adding 6 additional sources, two on the source line of the center grid to either side of the main optical axis Z and 4 other sources (shown as larger dots) placed on the four respective source lines between pairs of source lines of FIG. 5A. Adding more sources on given source line, that is, to more densely populate a given source line with more sources allows extraction of more tomographic information which may be helpful in bone removal image processing. This is illustrated in FIG. 5B), eg for a main view from an additional source sx added on the common source line sl2 in between sources s12 and s7. As a variant of the planar ASG grids as described above, reference is now made to FIG. 6 where a curved embodiment is shown.

Figure 6:
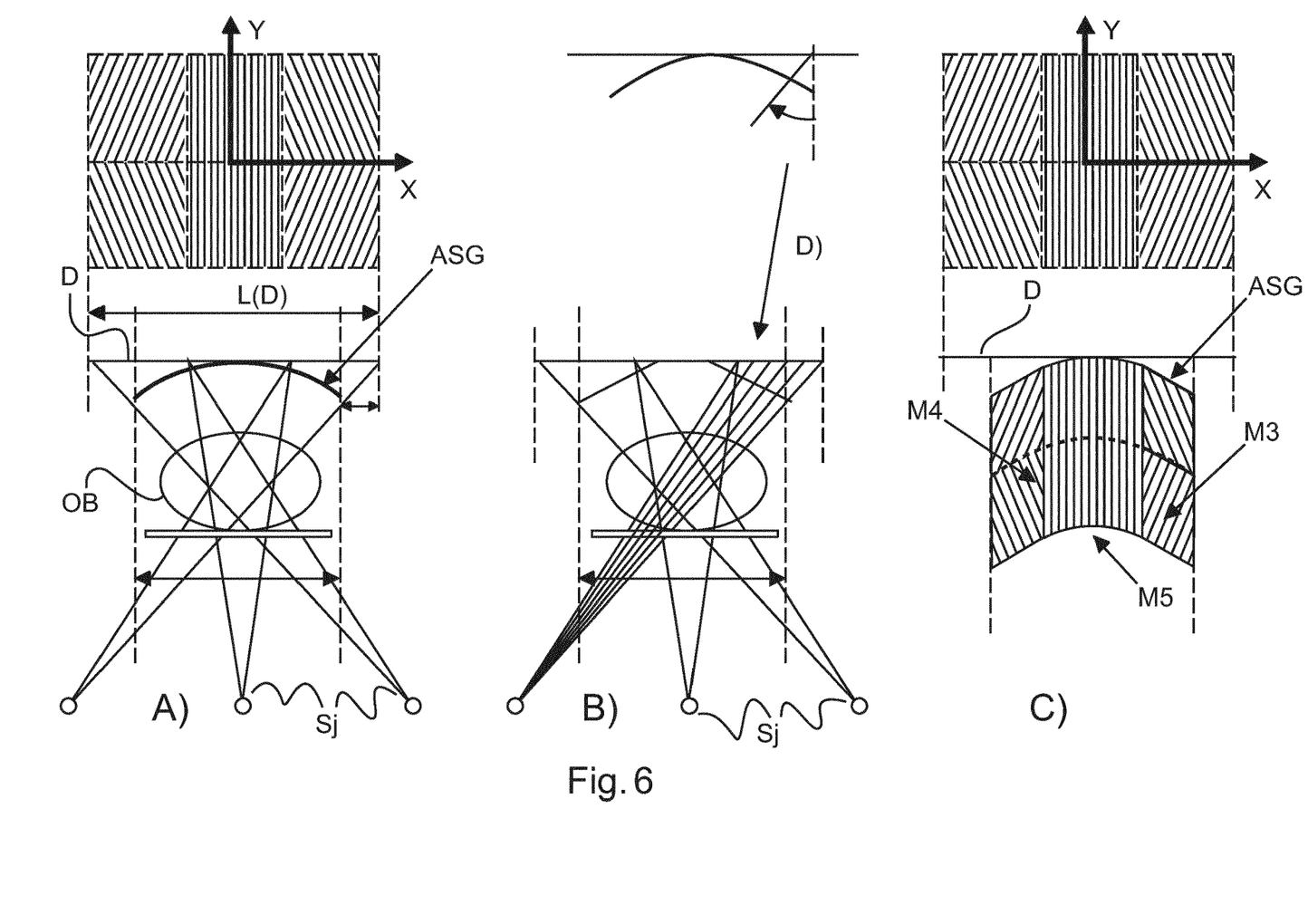

This curved ASG is similar to the ones discussed before otherwise to the ones before including a center grid and four outer grids M1-M4. The curved ASG grid is configured for use with detectors having a correspondingly curved surface.

FIG. 6A shows the curved construction versus a planar construction and illustrates the more compact built achievable as indicated by arrow L. The curved grid is shown in plan view (top) and in side elevation in X, Z plane (bottom) whilst in use in the imager IA.

FIG. 6C shows a plan view versus a perspective view of the curved grid as proposed herein, according to one embodiment. In the embodiment shown, it is only the center grid M5 that is curved whilst the peripheral grids M1-M4 are planar as before. The peripheral sub-grids M1-M4 are joined to the curved center grids at its straight pair of edges in tangential extension thereof (see bottom of FIG. 6C). Two sub-grids with different source line orientations are added to each side, with opposing pairs across the center grid having the same source line orientations similar to the previous embodiments FIG. 3-5. The center grid M5 is obtained using an initially flat sub-grid with only non-angulated strips and this is then bent about an axis parallel to its strips to achieve a symmetrical angulation throughout the strips. Rather than having the curved composite grid ASG constructed from a mix of curved and planar modules, other, "pure", embodiments are also envisaged where the ASG is curved throughout so is made up from curved modules only.

Pane 6B illustrates the manufactural advantage conferred by having a curved center sub-grid between planar sub-grids. As illustrated in the top part of FIG. 6B, the maximum inclination angle in the planar sub-grids can be reduced because the curvature of the center grid adds an additional angulation component. As will be appreciated and as shown in FIG. 2, the inclinations/angulations grow proportionally towards the outer portion in each sub-grid with the outermost strip having the strongest inclination. The inclination of the outermost strip is called the maximum inclination for the grid. Having a curved grid then allows increasing this maximum angle which is easier to produce.

Figure 7:
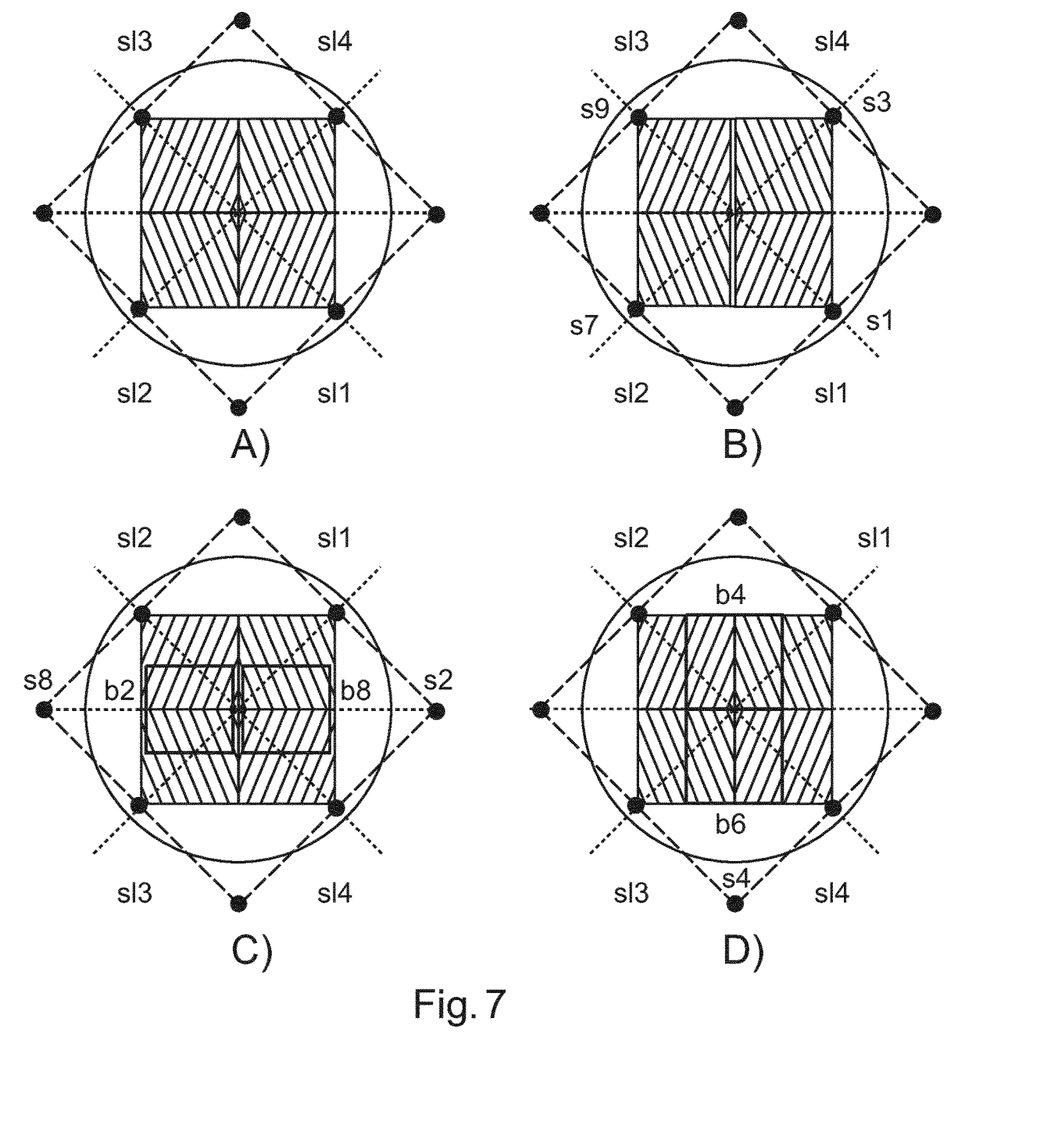

Whilst all the above embodiments include a (symmetric) center grid, this is not necessarily the case for all embodiments as shown in FIG. 7.

Figure 8:
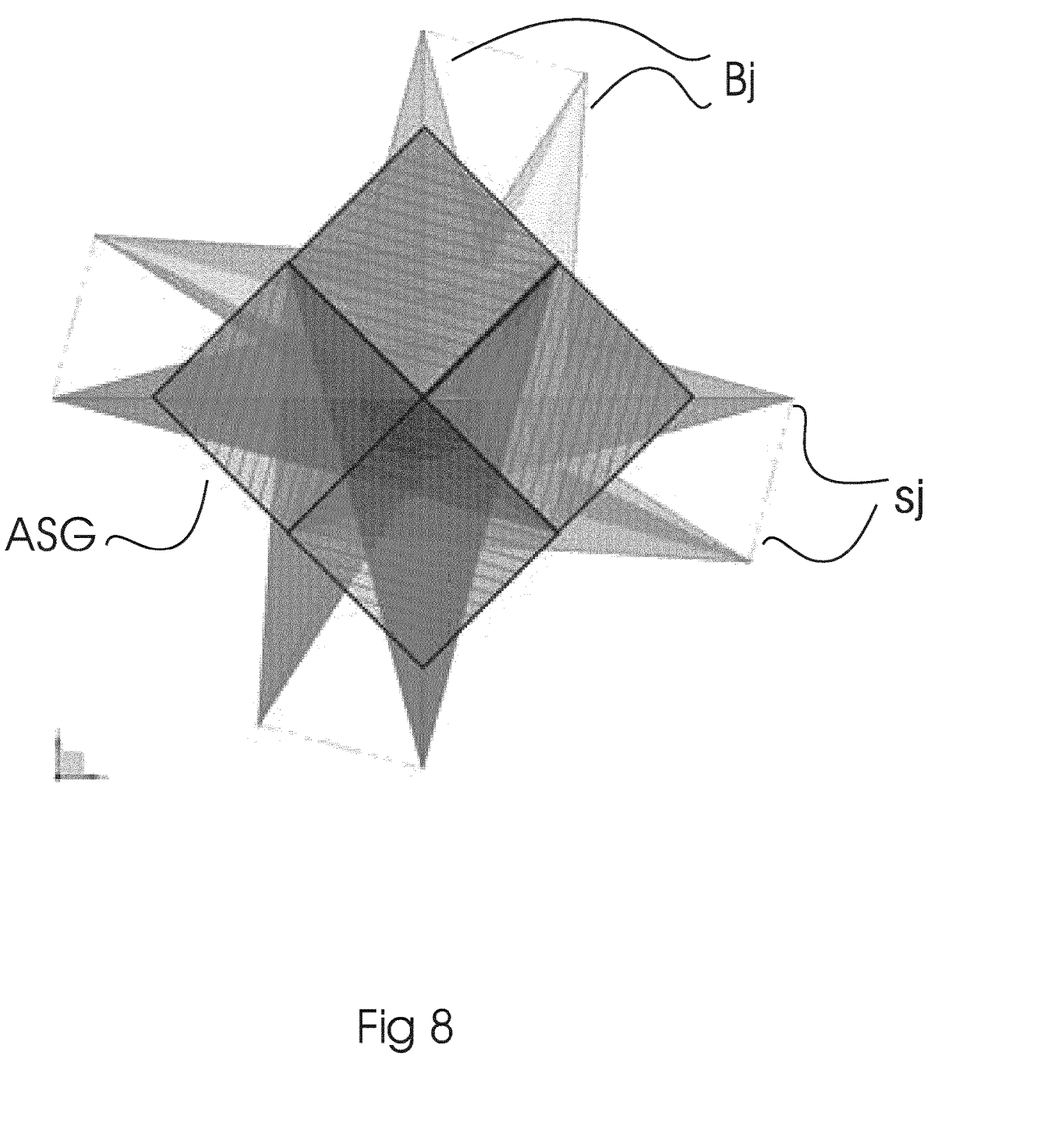

FIG. 7A shows a planar ASG as envisaged herein as having four sub-grids M1-M4 arranged as 4 quadrants around a center. There is no center grid as before. The grid defines four source lines that intersect to form quadrangular, such as a rectangle, or, specifically in this case, a square. FIGS. 7B-7D show different irradiation areas bj as produced by the corresponding sources sj. Sources s8 and s2 and sources s6 and s4 are positioned on source line intersections and hence their respective beams use different portions from different sub-grids for joint filtering. For instance source s8 irradiates sub-grid M2 and M3 whilst source s2 irradiates grids M1,M4 and so on. There is no grid sharing for sources s1, s3, s9 and s7 as shown in FIG. 7B. The irradiated areas b1,b7,b9 and b3 are coextensive with the irradiated sub-grid areas but this is not necessarily so in all embodiments as shown in FIG. 5B for instance, where the irradiated area b12 of source s12 is smaller than the total area of sub-grid M2, even in a non-grid sharing irradiation. FIG. 8 is a plan view from top along central axis Z on an ASG with a source configuration comprising 8 sources s1-s8 (indicated as sj in the FIG. 8). These are arranged in two squares, with two sets of 4 sources each defining the respective vertices of the two squares. The two square sub-configurations are rotated relative to each other by about 10°-15° around axis Z to obtain the configuration shown in FIG. 8. Variants of the above are also envisaged, such as configurations made up from more than two squares and/or where two or more squares are rotated by any other angle relative to each other. None of the above is restricted to squares however as any other polygon source arrangement with number of vertices ≥3 (such as triangles, pentagons, etc) are also envisaged herein. Preferably, but not necessarily, the polygons are regular (eg, as above square, or isosceles triangles, etc) to achieve at least quasi-isotropic source geometry for the reasons explained above.

In all of the above embodiments FIGS. 3-7, 8, if the ASG is planar (ie, all modules lie in a common plane), not all modules are symmetric. There is at least one (such as four as in the above embodiments) asymmetric grid(s). However there are other embodiments envisaged that are at least partly curved, where all sub-grids Mj are symmetric. This allows achieving a very compact imager footprint. This may be advantageous for mobile (eg, wheeled) X-ray imagers.

The manufacturing of the ASG as proposed herein requires in general a specification of the imaging geometry of the imager in which it is to be used. In particular, the dimensions of the imager or its footprint must be known. More specifically, the general layout of the peripheral X-ray sources must be known and also whether an AP view is required. Also, the position of the detector relative to the X-ray sources has to be known. Given these geometric specifications, the required source lines can be computed and these can then be used to manufacture the sub-grids. From the location of the source line in 3D the required inclination angles, in particular the maximum inclination angle of the strips, can be computed.

In one embodiment, the strip is constructed as a monolithic structure, with the strips in the different module being part of one continuous super-strip that is bent, and angulated to lay out the required pattern. This shape is the filled with filler material to obtain the finished ASG. In a semi-monolithic approach, a number of strips are formed into a series of nested polygonal shapes of progressively growing size.

Preferably however, the grid is manufactured from the desired number of sub-grids each being produced separately by a series of strips angled as required and separated by the filler material. The sub-grids so fashioned are then joined (glued, etc) at their edges to form the composite ASG. In other words, the ASG is an assembly of sub-grids. Preferably sub-grids are so joined that there is no gap between neighboring strips from different sets and it is preferable to connect these by soldering etc to avoid passage of unfiltered radiation therethrough.

One way to produce a sub-grid is to use a planar working plate with a raised shoulder at one of its edges. The x-radiation-opaque strips STj are then stacked up against this shoulder in alternate fashion with buffer strips to so build up the sub-grid. Glue is interposed at the buffer strip/x-radiation-opaque strip-interface to glue this system of strips together. Strip-stack is then released from the working plate, cut (if need be) into the desired size to so obtain the ASG grid module Mj. Before or after application, the filler strips must be cut with a cutting tool at suitable angles to produce angled faces to which the x-radiation-opaque strips STj are then applied to so effect the angulation of the strips. Alternatively and preferably, a glue layer of sufficient thickness and pliability is applied to join the filler strips and the x-radiation-opaque strips and it is this glue layer that then accommodates the slight angulation of strips with respect to their immediate neighboring strips.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging apparatus, comprising:
   a plurality of X-ray sources;
   an X-ray detector; and
   an anti-scatter grid comprising at least two grid modules;
   each grid module comprising a plurality of linear radiation-opaque strips, each strip having a longitudinal axis, wherein the strips of the different grid modules have the respective longitudinal axes that are not parallel to each other.

2. The X-ray imaging apparatus according to claim 1, wherein at least one strip of a grid module is slanted around the longitudinal axis relative to another strip of the grid module.

3. The X-ray imaging apparatus according to claim 1, wherein the strips of a grid module form a plane.

4. The X-ray imaging apparatus according to claim 1, wherein the strips of a grid module form a curved surface.

5. The X-ray imaging apparatus according to claim 1, wherein the at least two grid modules are arranged in a common plane.

6. The X-ray imaging apparatus according to claim 1, wherein the respective longitudinal axes of the strips from different grid modules form a polygon.

7. The X-ray imaging apparatus according to claim 1, wherein the anti-scatter grid is arranged in front of the X-ray detector.

8. The X-ray imaging apparatus according to claim 1, wherein the at least three X-ray sources are configured to emit respective X-ray beams towards the X-ray detector, and wherein the at least three X-ray sources are arranged around an optical axis of the X-ray detector.

9. The X-ray imaging apparatus according to claim 1, wherein the at least three X-ray sources can be positioned on a plane that does not intersect the X-ray detector.

10. The X-ray imaging apparatus according to claim 1, wherein the anti-scatter grid is configured to directionally filter X-ray beams generated by the plurality of the X-ray sources.

11. The X-ray imaging apparatus according to claim 10, wherein at least one of the beams irradiates the strips of the different grid modules.

12. The X-ray imaging apparatus according to claim 2, wherein the strips are slanted relative to each other so as to focus the anti-scatter grid to a line passing through a focal spot of at least one of the X-ray sources.

13. The X-ray imaging apparatus according to claim 1, wherein the strips of the different grid modules are focused to different lines passing through focal spots of the different X-ray sources.

14. The X-ray imaging apparatus according to claim 1, wherein the strips of the different grid modules are focused to different lines that intersect at a focal spot.

* * * * *